US012390576B2

(12) United States Patent
McCullough et al.

(10) Patent No.: US 12,390,576 B2
(45) Date of Patent: Aug. 19, 2025

(54) TAKE-HOME DRUG DELIVERY SYSTEM

(71) Applicant: AMGEN INC., Thousand Oaks, CA (US)

(72) Inventors: Adam B. McCullough, Westlake Village, CA (US); Sarah M. Korman, Los Angeles, CA (US); Nicholas J. Clark, Thousand Oaks, CA (US); Rafi Muhammad Sufi, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 403 days.

(21) Appl. No.: 16/787,077

(22) Filed: Feb. 11, 2020

(65) Prior Publication Data
US 2020/0254173 A1 Aug. 13, 2020

Related U.S. Application Data

(60) Provisional application No. 62/804,543, filed on Feb. 12, 2019.

(51) Int. Cl.
*A61M 5/00* (2006.01)
*A61B 46/10* (2016.01)
(Continued)

(52) U.S. Cl.
CPC ............. *A61M 5/002* (2013.01); *A61B 46/10* (2016.02); *A61M 5/1411* (2013.01);
(Continued)

(58) Field of Classification Search
CPC ............. A61M 5/002; A61M 5/16813; A61M 5/1411; A61M 5/142; A61M 5/178;
(Continued)

(56) References Cited

U.S. PATENT DOCUMENTS 1,859,316 A * 5/1932 Sponsel ................ A61M 5/002
206/229
3,292,776 A * 12/1966 Penn ..................... A61M 5/002
206/804

(Continued)

FOREIGN PATENT DOCUMENTS

| CN | 101172076 A | * | 5/2008 | |
| EP | 1003549 A1 | | 5/2000 | |
| WO | WO-2017106247 A1 | * | 6/2017 | ............ A61J 7/0409 |

OTHER PUBLICATIONS

International Application No. PCT/US2020/017574, International Search Report and Written Opinion, mailed May 12, 2020.

*Primary Examiner* — Nathan R Price
*Assistant Examiner* — Mark A Igel
(74) *Attorney, Agent, or Firm* — MARSHALL, GERSTEIN & BORUN LLP; Michael P. Furmanek

(57) ABSTRACT

A take-home drug delivery system includes a kit container defining an inner volume, a drug delivery container preparation assembly at least partially disposed within the inner volume of the kit container, and a sterile drape at least partially disposed within the inner volume of the kit container. The drug delivery container preparation assembly includes at least a drug delivery container, a drug vial containing a drug to be administered, a tubing set, and a drug delivery container mounting apparatus. The sterile drape includes a placement legend illustrated thereon.

18 Claims, 5 Drawing Sheets

(51) Int. Cl.
*A61M 5/14* (2006.01)
*A61M 5/142* (2006.01)
*A61M 5/168* (2006.01)
*A61M 5/178* (2006.01)
*A61M 39/10* (2006.01)

(52) U.S. Cl.
CPC ........ *A61M 5/142* (2013.01); *A61M 5/16813* (2013.01); *A61M 5/178* (2013.01); *A61M 39/10* (2013.01); *A61M 2039/1077* (2013.01); *A61M 2205/6063* (2013.01); *A61M 2205/6072* (2013.01); *A61M 2209/082* (2013.01)

(58) Field of Classification Search
CPC .......... A61M 39/10; A61M 2039/1077; A61M 2205/6083; A61M 2205/6072; A61M 2209/082; A61B 46/10
See application file for complete search history.

(56) References Cited

U.S. PATENT DOCUMENTS

| | | | | |
|---|---|---|---|---|
| 4,128,173 A | * | 12/1978 | Lazarus | A61B 17/3415 206/362 |
| 4,523,679 A | * | 6/1985 | Paikoff | A61B 50/33 206/439 |
| 5,324,258 A | * | 6/1994 | Rohrbough | A61M 5/162 604/86 |
| 5,529,189 A | * | 6/1996 | Feldschuh | A61M 5/31511 604/184 |
| 5,910,135 A | * | 6/1999 | Hadzic | A61M 39/286 604/251 |
| 2002/0177837 A1 | * | 11/2002 | Barnitz | A61M 5/142 604/416 |
| 2002/0185406 A1 | * | 12/2002 | Massengale | A61B 50/30 206/570 |
| 2009/0318893 A1 | * | 12/2009 | English | A61M 5/162 604/83 |
| 2011/0306928 A1 | * | 12/2011 | Duncan | A61M 5/002 604/93.01 |
| 2012/0041338 A1 | * | 2/2012 | Chickering, III | A61B 5/417 604/173 |
| 2013/0237915 A1 | * | 9/2013 | Barrelli | B65D 83/0061 604/136 |
| 2014/0155827 A1 | * | 6/2014 | Ostrander | G16H 10/65 604/93.01 |
| 2014/0357304 A1 | * | 12/2014 | Ostrander | H04W 4/023 455/456.3 |
| 2016/0239610 A1 | * | 8/2016 | Andersen | G16H 10/60 |
| 2016/0271015 A1 | * | 9/2016 | Wengreen | A61J 1/165 |
| 2018/0110918 A1 | * | 4/2018 | Tennican | A61M 5/008 |

* cited by examiner

TAKE-HOME DRUG DELIVERY SYSTEM

CROSS-REFERENCE TO RELATED APPLICATION

Priority is claimed to U.S. Provisional Patent Application No. 62/804,543, filed Feb. 12, 2019, the entire contents of which are hereby incorporated herein by reference.

FIELD OF DISCLOSURE

The present disclosure generally relates to drug delivery devices and, more particularly, to take-home drug delivery systems.

BACKGROUND

Drugs are administered to treat a variety of conditions and diseases. Intravenous ("IV") therapy is a drug dosing process that delivers drugs directly into a patient's vein using an infusion contained in a delivery container (e.g., a pliable bag). These drug dosings are typically performed in a healthcare facility, though these facilities may not meet all of a patient's needs or requirements. Oftentimes, due to scheduling or other constraints, a patient may miss a large number of drug dosings due to their inability to devote a significant portion of their time traveling to a healthcare facility for treatment. Additionally, the steps required to administer a drug are typically complex due to a need to preserve a safe, sterile environment, and to ensure the correct quantities of drug ingredients are ultimately administered.

As described in more detail below, the present disclosure sets forth systems and methods for take-home drug delivery system embodying advantageous alternatives to existing systems and methods, and that may address one or more of the challenges or needs mentioned herein, as well as provide other benefits and advantages.

SUMMARY

In accordance with a first aspect, a take-home drug delivery system can include a kit container, a drug deliver container preparation assembly, and a sterile drape. The kit container defines an inner volume. The drug delivery container preparation assembly is at least partially disposed within the inner volume of the kit container. The drug delivery container preparation assembly includes at least the following components: a drug delivery container, a drug vial containing a drug to be administered, a tubing set, and a drug delivery container mounting apparatus. The sterile drape is at least partially disposed within the inner volume of the kit container, and includes a placement legend illustrated thereon.

In some forms, the sterile drape can include a film or sheet of sterile material.

In some forms, the placement legend can include a visual representation of relative locations for placing the components of the drug delivery container preparation assembly.

In some forms, the sterile drape can include a plurality of sterile drapes, each including a placement legend illustrated thereon.

In some forms, the system can further include preparation and administrations instructions.

In some forms, the preparation and administrations instructions are provided on the sterile drape or on a separate pamphlet in the kit container.

In some forms, the system can further include a machine readable code illustrated on the sterile drape and providing access to the preparation and administration instructions.

In some forms, the drug delivery container preparation assembly can further include at least one of: i) an elastomeric pump including a drug reservoir, ii) at least one of a saline bag or a bottle, and iii) a syringe, wherein the take-home drug delivery system further comprises a syringe driver.

In some forms, the system can further include a pump preparation assembly including at least one of a pump, a rate controller, an inline drip chamber, or a roller-clamp.

In some forms, the system can further include a PICC line extender.

In some forms, the system can further include a drug vial adapter adapted to facilitate transfer of the drug contained in the drug vial to the drug delivery container.

In some forms, the drug vial adapter can include at least one of a CSTD or a syringe and needle assembly.

In some forms, the system further can include a sanitization assembly.

In some forms, the system further can include a disposal assembly.

In some forms, the disposal assembly can include at least one of a sharps container, a disposal bag, or sterilizing wipe.

In some forms, the system can further include a bulk preparation assembly, the bulk preparation assembly including at least one of disposable gloves, a sterile wipe, or a sanitizer.

In some forms, the bulk preparation assembly is provided as an add-on unit packaged separately from the kit container.

In accordance with another aspect, a method for preparing a take-home drug delivery system can include providing a kit container defining an inner volume. The method can also include at least partially disposing a plurality of components of a desired drug delivery container preparation assembly within the inner volume of the kit container, the desired drug delivery container assembly selected from a plurality of selectable drug delivery container preparation assemblies. The method can also include at least partially disposing a sterile drape within the inner volume of the kit container, the sterile drape including a placement legend illustrated thereon.

In some forms, the sterile drape can include a film or sheet of sterile material.

In some forms, the placement legend can include a visual representation of relative locations for the components of the drug delivery container preparation assembly, and further comprising.

In some forms, disposing the sterile drape within the inner volume of the kit container can include disposing a plurality of sterile drapes, each including a placement legend illustrated thereon, within the inner volume of the kit container.

In some forms, the method can further include providing access to preparation and administrations instructions in the inner volume of the kit container.

In some forms, providing access to the preparation and administrations instructions comprises providing the preparation and administrations instructions on the sterile drape or on a separate pamphlet in the kit container.

In some forms, providing access to the preparation and administrations instructions comprises providing a machine readable code illustrated on the sterile drape, which directs a user to the preparation and administration instructions.

In some forms, the each of the plurality of selectable drug delivery container preparation assemblies can include: a drug delivery container; a drug vial containing a drug to be administered; a tubing set; and a drug delivery container mounting apparatus.

BRIEF DESCRIPTION OF THE DRAWINGS

The above needs are at least partially met through provision of the systems and approaches for a take-home drug delivery device described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Turning to the figures, pursuant to these various embodiments, a take-home drug delivery system 100 or kit and a corresponding method 200 of preparing a take-home drug delivery system 100 are provided. The take-home drug delivery system 100 can be used by a healthcare professional, a caregiver, or patient to prepare a drug delivery device to be delivered to a patient. The drug delivery system 100 provides a patient and customer-centric system for drug delivery that avoids compromising safety and efficacy. The drug delivery system 100 may be used by patients having existing, reliable access to a drug delivery line such as an IV, a PICC line, a central line, and/or an implanted port. The system 100 may be used to provide intravenous, subcutaneous, intra-arterial, intramuscular, and/or epidural delivery approaches. By using the system 100, patient anxiety and or confusion may be reduced due to reduced preparation complexity and wait times caused by the drug preparation process.

Figure 1:
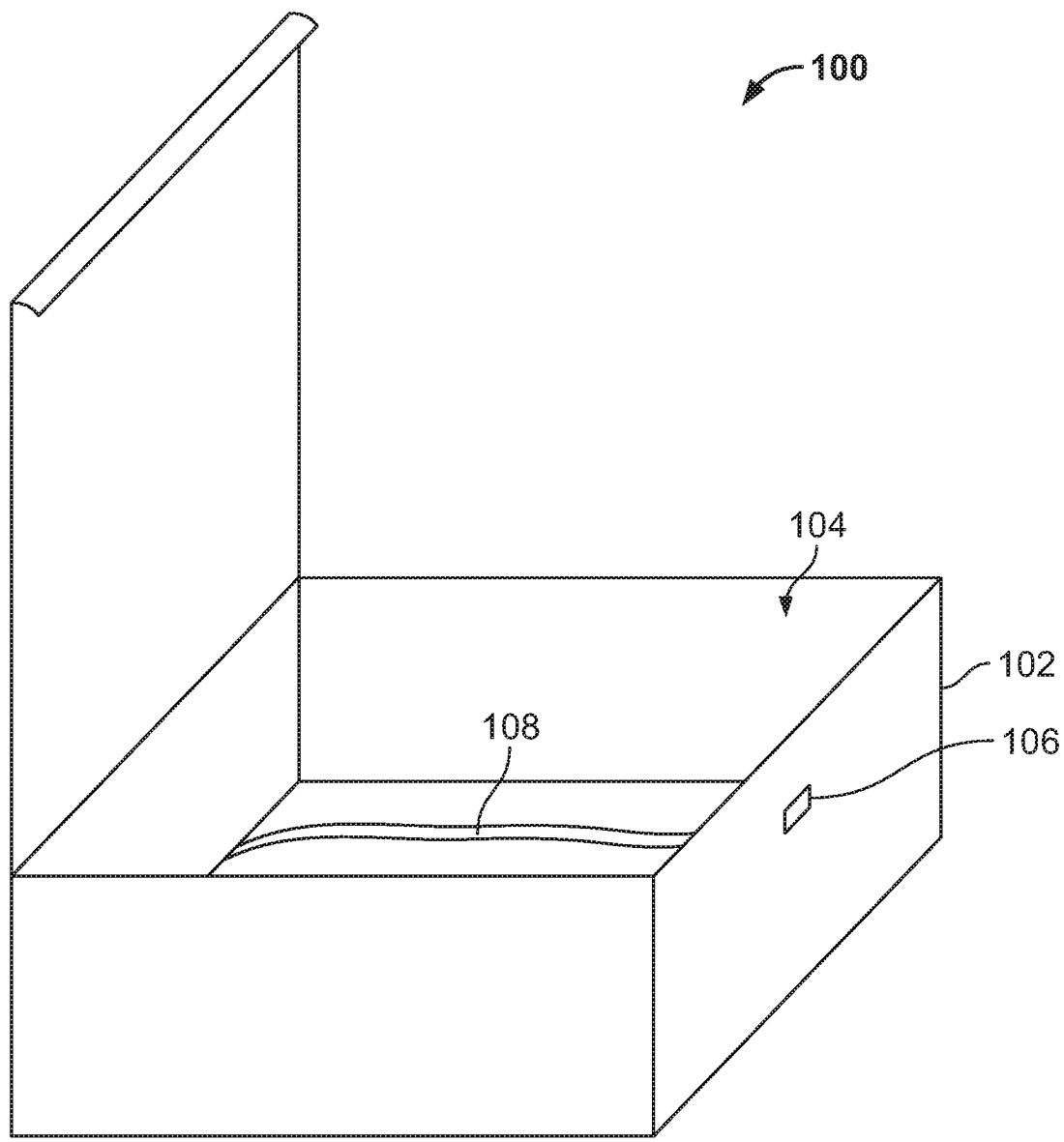
FIG. 1 illustrates a perspective view of an example take-home drug delivery system in accordance with various embodiments.
Figure 2:
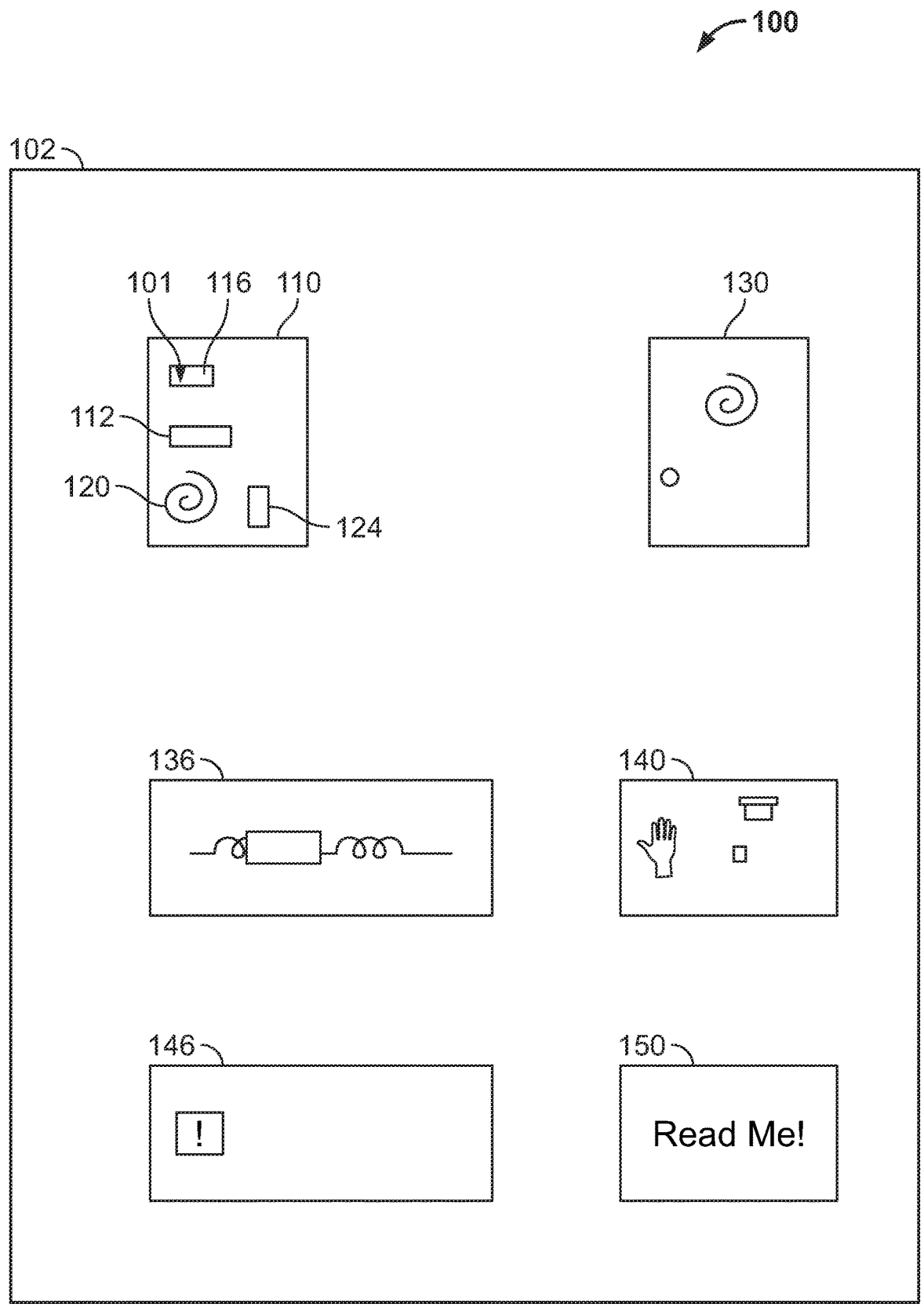
FIG. 2 illustrates a schematic view of the example take-home drug delivery system of FIG. 1 in accordance with various embodiments.
Figure 3:
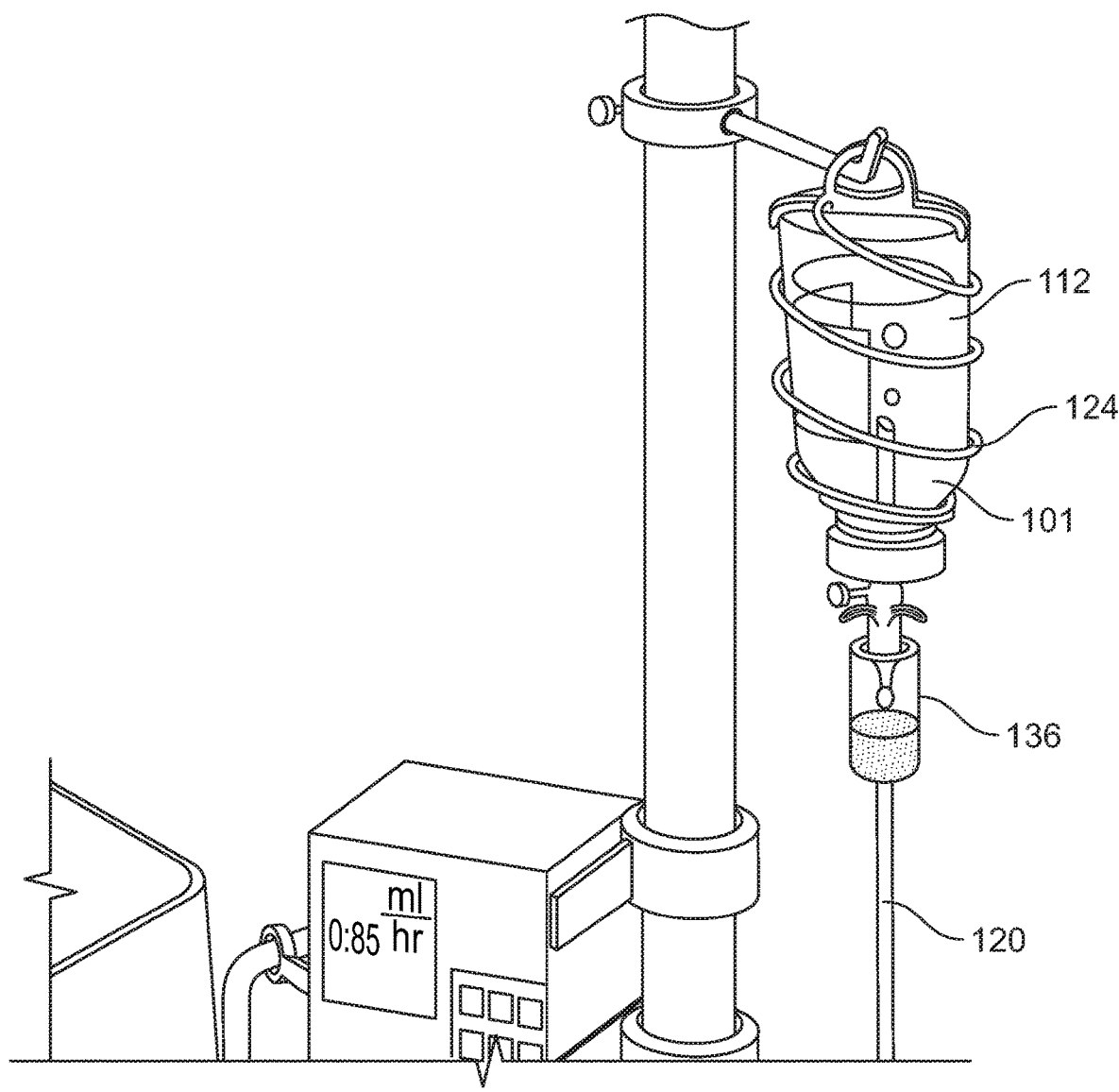
FIG. 3 illustrates an example usage configuration for the take-home drug delivery system of FIG. 1 in accordance with various embodiments.

Generally, the system 100 includes any number of ingredients needed for drug administration. For example, sterile components, components and/or techniques used to maintain a sterile field, medication, a delivery mechanism, and/or components to access and maintain delivery line access points are all included in the system 100. The system 100 may additionally include instructions and/or tools for disposing the contents of the kit in a safe manner. With reference to FIGS. 1-3, the system 100 includes a kit container 102, a drug delivery container preparation assembly 110, and a sterile drape 150.

The kit container 102 may be in the form of a box or case that defines an inner volume 104 to safely place and transmit the components of the system 100. The kit container 102 may include a closure member 106 such as a lock, seal, tamper-resistant device, and/or any other mechanism. The inner volume 104 of the kit container 102 may include any number of additional features to assist in safe transit of the components such as securement features (e.g., straps, tie-downs, etc.) 108, padding, partitions, and the like. Other examples are possible. The kit container 102 may include a window and/or a label region to identify the particular drug product contained therein.

The drug delivery container preparation assembly 110 includes a number of ingredients used to prepare the drug for administration. For example, the drug delivery container preparation assembly 110 may include a drug delivery container 112, a drug vial 116 containing a drug 101 to be administered, a tubing set 120, and a mounting apparatus 124. The drug delivery container preparation assembly 110 may include any number of additional components such as saline solutions, reconstituting solutions contained in containers, vials, syringes, adapters, and the like. The drug delivery container 112 may be in the form of an elastomeric pump (e.g., a balloon or "grenade"-style device having an internal reservoir), a saline container (e.g., a bag and/or a rigid or semi-rigid bottle such as glass, CZ, or a custom blow-fill seal), or a syringe assembly.

The drug delivery container 112 may include a number of ports (e.g., inlets and/or outlets) having a number of coupling mechanisms that allow for the drug 101 and other ingredients to be selectively inserted into (e.g., during an admixing process) and withdrawn from the drug delivery container 112 for dosing. For example, the drug delivery container preparation assembly 110 may include any number of adapters that can be used to transfer fluids in a stable environment from various components such as the drug vial 116. In some examples, a leur locking mechanism may be used where a syringe and needle assembly is coupled to desired components (e.g., the drug delivery container 112 and/or the drug vial 116) for fluid transfer. In other examples, a closed system transfer device ("CSTD") may be used. In these examples, the CSTD may be coupled directly to one or ones of the drug delivery container 112 and/or the drug vial 116. Additional example elastomeric pump containers and associated features are described in U.S. Appln. No. 62/804,447, filed on Feb. 12, 2019, the contents of which are incorporated by reference in their entirety.

In some examples, the drug vial 116 may be in a lyophilized form that requires reconstitution prior to the admixing process. In any or all of these drug delivery containers 112, a number of ingredients may be prefilled so as to reduce the overall footprint of the take-home drug delivery system 100 and to allow for an easier preparation and/or administration process. In such a kit, the drug delivery container 112 may come prefilled with a saline solution and/or an IV stabilizing solution ("IVSS") so as to only require a minimal number of drug reconstitution steps. Examples and/or alternative systems and approaches for preparing (i.e., reconstituting) drug delivery containers 112 are described in U.S. Appln. No. 62/804,478, filed on Feb. 12, 2019, the contents of which are incorporated by reference in their entirety.

The mounting apparatus 124 may be any suitable device capable of retaining the drug delivery container 112 in a desired position. For example, the mounting apparatus 124 may be in the form of a reusable cage constructed from a plastic or any other material that is positioned about a periphery of the drug delivery container 112. In some examples, the mounting apparatus 124 may be constructed from a resilient material that wraps around all or a portion of the drug delivery container 112 (see, e.g., FIG. 3), which, as previously noted, may be a rigid or semi-rigid bottle. The mounting apparatus 124 may be mounted to a support pole or other structure using any number of approaches.

The tubing 120 couples to the drug delivery container 112 using any number of approaches, and is ultimately coupled to the patient's drug delivery port to administer the drug 101. The tubing 120 may be in the form of a universal tubing set, or may be a custom tubing set having components allowing for flow control coupled thereto. The system 100 may include an optional drug delivery port assembly 130 that includes components to assist in the safe coupling of the tubing 120 to the patient. Some of the drug delivery port assembly 130 components may be disposed along the tubing 120 may be any number of components used to ensure that proper transmission of the drug 101 is achieved such as any number or combination of IV-line spikes, clamps, caps, saline flushes (which, in some examples, may be sterile pre-filled saline syringes), and the like. In some examples, the drug delivery port assembly 130 may include a PICC line extender that provides a patient with extra mobility to use both hands during drug administration. For example, an approximately 0.2 m to approximately 1.0 m length of tubing may be provided that includes a male to female luer lock connector on one end, and a female to male adapter on the other end. Other examples are possible.

In some examples, the delivery container preparation assembly 110 may be in the form of a specialty container having custom reconstitution components. For example, any number of components provided in Pfizer Injectables' ADD-Vantage drug reconstitution system may be provided in the system 100. Other examples are possible.

The system 100 may further include an optional pump assembly 136 that assists in ensuring the drug 101 is delivered to the patient at a correct flow rate. As previously noted, the drug delivery container 112 may be in the form of an elastomeric pump in lieu of a traditional IV delivery bag. However, in some examples, by providing an inline drip chamber and mounting or hanging the drug delivery container 112 via the mounting apparatus 124, a low-cost solution for measuring and partially controlling the flow rate of the drug 101 is achieved. In some examples, treatment profiles may be individually analyzed by assessing a risk of this approach to determine the required flow rate accuracy. In some examples, a roller-clamp or other controllable flow restriction may be pre-installed in or on the tubing 120 to allow for selective adjustment of the flow rate based on a number of drips per minute and the prescribed infusion (or drug delivery) rate.

In yet other examples, the pump assembly 136 may be in the form of a flow rate monitor that can monitor and adjust the flow rate of the drug 101 during drug administration. Example flow rate monitors and associated features are described in U.S. Appln. No. 62/804,506, filed on Feb. 12, 2019, the contents of which are incorporated by reference in their entirety.

In yet other examples, the pump assembly 136 may be in the form of a disposable or reusable syringe driver such as the Freedom 60 syringe driver. In some examples, a flow restrictor may be incorporated to assist in operation of the syringe driver. In these examples, by using a syringe as the reservoir (as opposed to an IV bag, a bottle, and/or an elastomeric container), may provide for predicable control of the medication based on the fluid viscosity of the drug 101, the particular tubing 120 used, the presence of any filters or other components, the volume of the drug 101, a drive force of the syringe driver, and/or any other measureable or designed flow restriction elements (e.g., small bore stainless steel tubings). In some examples, a universal spring driven syringe driver pump assembly 136 may be provided that allows for user adjustment and potentially avoids the need for multiple SKUs. In still other examples, the pump assembly 136 may be in the form of an electronic peristaltic pump that may selectively compress or relax the tubing 120 to adjust the flow rate of the drug 101.

The optional pump assembly 136 may include any number of additional components such as secondary tube sets, roller clamps, and the like.

The system 100 may additionally include an optional sanitization assembly 140 that includes any number of components used to ensure the environment and the components in the system 100 remain properly sterile. For example, the sanitization assembly 140 may include any number of gloves, hand sanitizer, sterile caps, alcohol wipes, closure assemblies for end-of use procedures (e.g., a PICC line closure system having a line flush, sanitizers, caps, etc.) and the like.

The system 100 may include an optional disposal assembly 146 for safe disposal of the components therein. For example, the disposal assembly 146 may include components such as a sharps container, any number of biohazard bags depending on the drug being administered (e.g., red or yellow biohazard bags), additional hand sanitizer, and the like. Additional components are possible.

Figure 4:
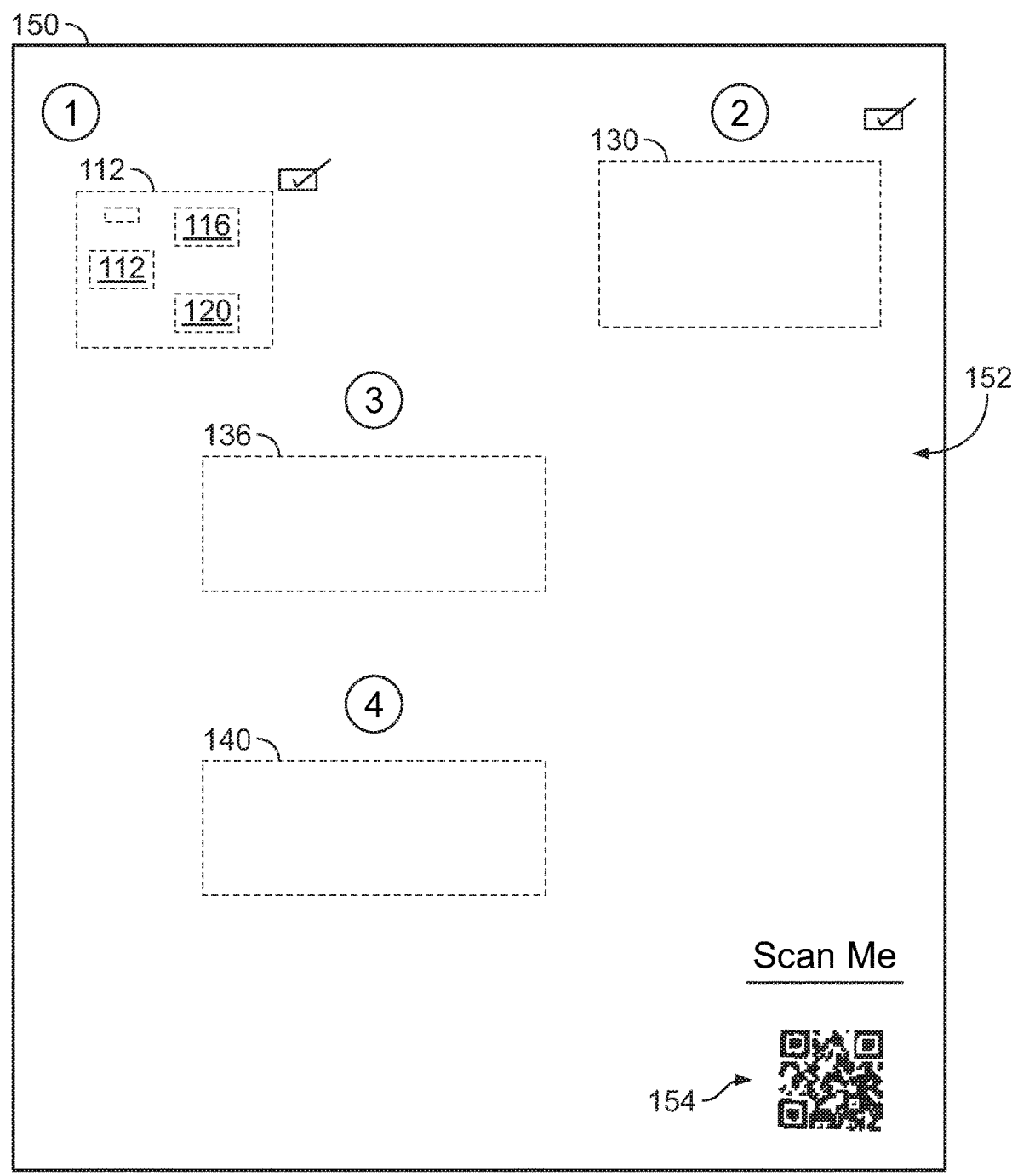
FIG. 4 illustrates an example sterile drape of the example take-home drug delivery system of FIGS. 1 and 2 in accordance with various embodiments.

The sterile drape 150 is used to facilitate a clear layout for placement of components used to administer the drug 101. The sterile drape 150 may be in the form of a sheet or film that provides a visual representation of relative locations of the different components and/or assemblies of the system 100. For example, as illustrated in FIG. 4, the sterile drape 150 illustrates a placement legend 152 that is sized and dimensioned for a particular take-home drug delivery system 100. The placement legend 152 illustrates relative placement of the components for efficient preparation. The illustrated sterile drape 150 is used for a system 100 that includes a drug delivery container preparation assembly 110, a drug delivery port assembly 130, a pump assembly 136, and a sanitization assembly 140. Any number of different sterile drapes 150 may be used that include different layouts and component placement legends 152 as required.

The sterile drape 150 further includes instructions or an instruction link 154 that provide clear directions for preparing and administering the drug 101. In some examples, the instruction link 154 may be in the form of a QR code that a user may access via computing device (e.g., a cellular telephone, a tablet, a computer, etc.). In other examples, the instruction link 154 may be a printed pamphlet or may be printed directly on the sterile drape 150. In some approaches, the sterile drape 150 may include checkboxes or other completion indicators that a user may mark off upon completing a preparation or administration step so as to assist in patient confidence that they are properly preparing and/or administering the drug 101.

Any number of distinct drug delivery container preparation assembly 110 may be included in the system 100 that can include different components depending on the intended delivery environment, the drug being administered, particular use requirements, and the like. In other words, any number of different systems 100 may be stocked to allow for quick selection by healthcare professionals. In some forms, a healthcare professional may input particular patient prescribing information, requirements and/or characteristics into a computing device having a database that includes defining characteristics of the different systems 100, and the computing device may automatically identify a particular system 100 to be provided to the patient.

Figure 5:
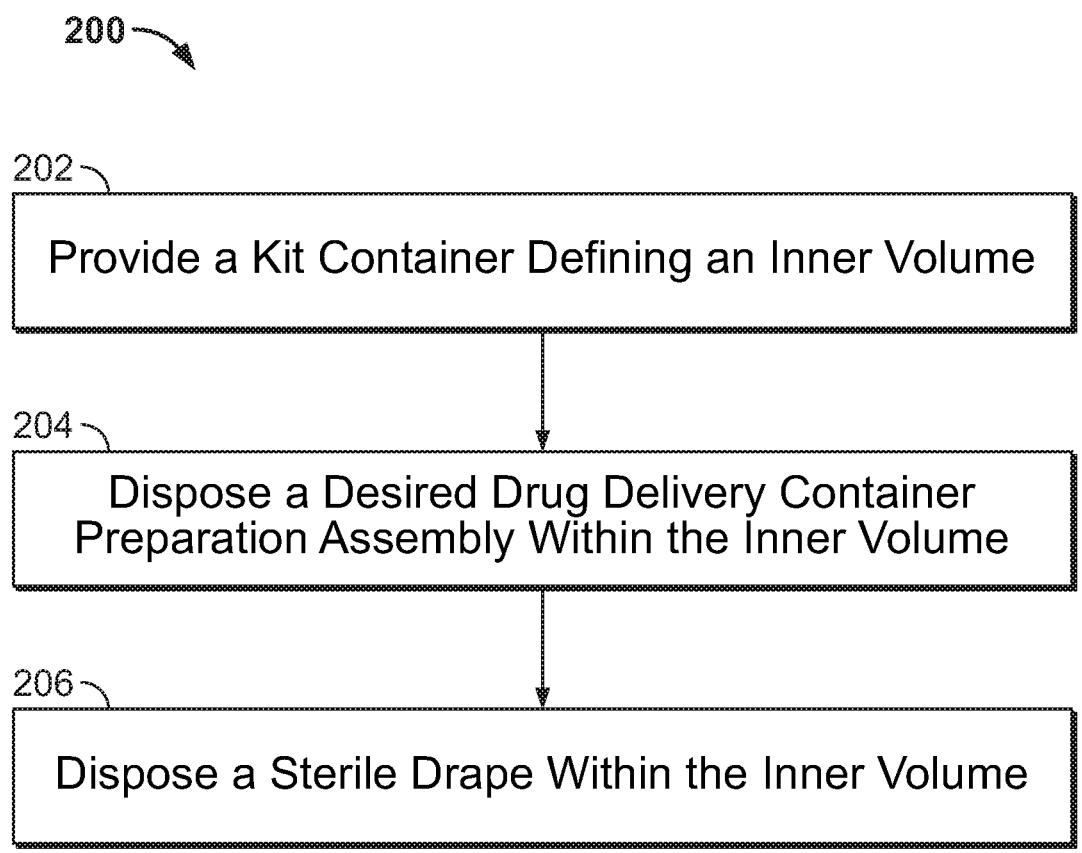
FIG. 5 illustrates an example approach for preparing the take-home drug delivery system of FIGS. 1-3 in accordance with various embodiments.

In some forms, a healthcare professional may select and build the desired kit based on a patient's needs. An approach 200 may include providing (FIG. 5 at step 202) a kit container and disposing the desired components (e.g., a particular drug delivery container preparation assembly 110 selected from a number of different drug delivery container preparation assemblies 110) into the inner volume of the kit container (FIG. 5 at step 204). A sterile drape may additionally be provided and included in the kit (FIG. 5 at step 206). Accordingly, in these examples, a healthcare professional may easily and quickly assemble a system 100 for a patient.

So configured, any number of distinct systems 100 that have different assemblies, subassemblies, and components within these assemblies and subassemblies may be stocked by a manufacturer and/or a healthcare professional. Once a healthcare professional identifies the correct system 100 to use (based on the particular patient's drug delivery regimen), the time required to prepare and administer the drug 100 is greatly reduced. Further, by providing a system 100 having minimal user requirements and clear instructions, patients, clinicians, and/or caregivers may confidently administer the drug without fear of infection and/or embolism and while avoiding other risks associated with the medicine being used. Advantageously, the system 100 may be picked up at a healthcare facility (e.g., a clinic), and may include accompanying patient support and/or information so that the patient needn't spend significant time at the facility on a regular basis. In other examples, an online delivery service may be used to ship the system 100 to the patient at desired intervals, thereby eliminating an additional step for the patient.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

In some embodiments, the reservoir of the drug delivery device may be filled with or the device can be used with bispecific T cell engager (BITE®) antibodies such as but not limited to BLINCYTO® (blinatumomab) in varying quantities such as dosages between approximately 5 mcg/m²/day and approximately 15 mcg/m²/day. Additionally, the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-a4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A take-home drug delivery system comprising:
   a kit container defining an inner volume;
   a drug delivery container preparation assembly disposed within the inner volume of the kit container, the drug delivery container preparation assembly including at least the following components: a drug delivery container having one of a rigid or semi-rigid body with a length, a drug vial containing a drug to be administered, a tubing set, and a drug delivery container mounting apparatus configured to wrap around the body of the drug delivery container; and
   a sterile drape at least partially disposed within the inner volume of the kit container, the sterile drape including a visual representation of relative locations for placing the components of the drug delivery container preparation assembly for preparation.

2. The take-home drug delivery system of claim 1, wherein the sterile drape comprises a film or sheet of sterile material.

3. The take-home drug delivery system of claim 1, wherein the sterile drape comprises a plurality of sterile drapes, each including the placement legend illustrated thereon.

4. The take-home drug delivery system of claim 1, further comprising preparation and administrations instructions.

5. The take-home drug delivery system of claim 4, wherein the preparation and administrations instructions are provided on the sterile drape or on a separate pamphlet in the kit container.

6. The take-home drug delivery system of claim 5, further comprising a machine readable code illustrated on the sterile drape and providing access to the preparation and administration instructions.

7. The take-home drug delivery system of claim 1, wherein the drug delivery container preparation assembly further comprises at least one of:
   i) an elastomeric pump including a drug reservoir,
   ii) at least one of a saline bag or a bottle, and
   iii) a syringe, wherein the take-home drug delivery system further comprises a syringe driver.

8. The take-home drug delivery system of claim 1, further comprising a pump preparation assembly including at least one of a pump, a rate controller, an inline drip chamber, or a roller-clamp.

9. The take-home drug delivery system of claim 1, further comprising a PICC line extender.

10. The take-home drug delivery system of claim 1, further comprising a drug vial adapter adapted to facilitate transfer of the drug contained in the drug vial to the drug delivery container.

11. The take-home drug delivery system of claim 10, wherein the drug vial adapter comprises at least one of a closed system transfer device or a syringe and needle assembly.

12. The take-home drug delivery system of claim 1, further comprising a sanitization assembly.

13. A method for preparing a take-home drug delivery system, the method comprising:
   providing a kit container defining an inner volume;
   at least partially disposing a plurality of components of a desired drug delivery container preparation assembly within the inner volume of the kit container, the desired drug delivery container assembly selected from a plurality of selectable drug delivery container preparation assemblies and including a drug delivery container having a body and a drug delivery container mounting apparatus having a helical structure configured to wrap around the body of the drug delivery container; and
   at least partially disposing a sterile drape within the inner volume of the kit container, the sterile drape including a visual representation of relative locations for at least a drug delivery container, a drug vial, and a tubing set of the drug delivery container preparation assembly for preparation of the take-home drug delivery system to administer a drug.

14. The method of claim 13, wherein the sterile drape comprises a film or sheet of sterile material.

15. The method of claim 13, wherein disposing the sterile drape within the inner volume of the kit container comprises disposing a plurality of sterile drapes, each including the visual representation illustrated thereon, within the inner volume of the kit container.

16. The method of claim 13, comprising providing access to preparation and administrations instructions in the inner volume of the kit container.

17. The method of claim 16, wherein providing access to the preparation and administrations instructions comprises providing the preparation and administrations instructions on the sterile drape or on a separate pamphlet in the kit container.

18. The method of claim 17, wherein providing access to the preparation and administrations instructions comprises providing a machine readable code illustrated on the sterile drape, which directs a user to the preparation and administration instructions.

* * * * *